US007335781B2

(12) United States Patent
Yang et al.

(10) Patent No.: US 7,335,781 B2
(45) Date of Patent: *Feb. 26, 2008

(54) AMINOTHIOL COMPOUND

(75) Inventors: Teng-Kuei Yang, Taichung (TW); Shi-Liang Tseng, Taichung (TW); To Liu, Taichung (TW); Nan-Kuang Chen, Taichung (TW)

(73) Assignee: Huey Jiin Co., Ltd., Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 10/807,710

(22) Filed: Mar. 23, 2004

(65) Prior Publication Data

US 2004/0181057 A1 Sep. 16, 2004

Related U.S. Application Data

(63) Continuation-in-part of application No. 10/039,557, filed on Jan. 8, 2002.

(51) Int. Cl.
*C07D 207/04* (2006.01)
(52) U.S. Cl. ...................... 548/570; 548/400
(58) Field of Classification Search ............... 548/570; 544/106, 158; 546/184, 248
See application file for complete search history.

(56) References Cited

U.S. PATENT DOCUMENTS 6,861,536 B2 *  3/2005  Yang et al. .................. 548/570
6,965,038 B2 * 11/2005  Yang et al. .................. 548/570

OTHER PUBLICATIONS

Kang at al. 1994, 10:842-4, CAS 122:55341, Accession No. 1995;194984.*
Kang et al. 1996, 1135-142, CAS 126:131036, Accession No. 1997: 39785.*
Carreno et al.1990, 339-42,CAS 113:131411, Accession No. 1990: 531411.*
Trost et al (1982): STN International HCAPLUS database Columbus (OH), accession No. 1982: 217316.*

* cited by examiner

*Primary Examiner*—Golam M. M. Shameem
(74) *Attorney, Agent, or Firm*—Charles E. Baxley

(57) ABSTRACT

The present invention discloses an aminothiol compound having a general formula I wherein $R^1$-$R^5$ are substitutable ligands. Such compound can perform as a superior catalyst in an asymmetric addition reaction of organic metal compounds and aldehyde. According to the present invention, the aminothiol compound is needed only less than 0.02% based on main reactants to obtain enantioselectivity higher than 98% enantiomeric excess, whereby the asymmetric reactions can become very economic.

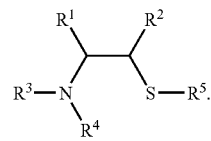

I

3 Claims, No Drawings

AMINOTHIOL COMPOUND

CROSS-REFERENCE TO RELATED APPLICATION

This is a CIP application of U.S. patent application Ser. No. 10/039,557 filed on Jan. 8, 2002, and for which priority is claimed under 35 U.S.C.sctn.120.

BACKGROUND OF THE INVENTION

1. Field of the Invention

The present invention relates aminothiol compounds which perform as superior catalysts in the asymmetric addition reactions of organic zinc and aldehyde.

2. Description of the Related Technology

For preparing secondary alcohols, one of the most important methods is to react organic zinc with aldehyde in addition reactions. In order to accelerate this reaction, chiral aminoalcohols are usually added as ligands to combine with organic zinc. Such chiral aminoalcohol create an asymmetric reaction environment, so that one of the produced chiral secondary alcohols is produced more than its stereoisomer, i.e., the asymmetric addition reactions. Apparently, the crux of obtaining a high chemical yield as well as enantioselectivity in the above reactions is to select proper chiral compounds which can provide excellent asymmetric environment for catalytical process.

Though many chiral compounds used in the addition reactions regarding organic zinc and aldehyde can achieve good enantioselectivity, however, these compounds have to be added at an amount at least 1% of the main reactants, and usually around 20%. Additionally, the enantioselectivity always decays with decreasing amount of the chiral ligands used. In general, the enantioselectivity is reduced below 90% enantiomeric excess (e.e.) when the chiral ligands are descended under 5%, so that most of above reactions are not good enough for industrial usage.

Aminoalcohols with optical activity, such as N,N-dibutylnorephe-edine, are frequently applied to accelerating the asymmetric addition reactions of organic zinc and aldehyde as chiral ligand catalysts. By adding aminoalcohols, enantioselectivity of the above reactions can be reached as high as 99% e.e., but an amount 10-20% of chiral aminoalcohols is need. Therefore, it's an important issue how to reduce the necessary amount of the chiral ligands used in the catalysis, so that it can be an economically efficient process

SUMMARY OF THE INVENTION

The object of the present invention is to provide aminothiol compounds with two chiral centers, which can increase enantioselectivity of asymmetric addition of organic zinc and aldehyde.

In order to achieve the above object, the present invention discloses an aminothiol compound having a general formula I;

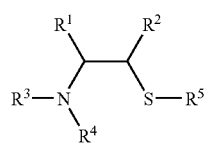

wherein $R^1$-$R^5$ are substitutable ligands.

According to the present invention, the aminothiol compounds can perform as superior catalysts in asymmetric addition reactions wherein organic zinc and aldehyde are involved. In such reactions, though the catalysts are added only 0.1% or even 0.02%, enantioselectivity higher than 98% e.e. can always be obtained. Such catalyses are economically useful for industries.

DETAILED DESCRIPTION OF THE PREFERRED EMBODIMENTS

In the present invention, aminothiol compounds have a general formula I,

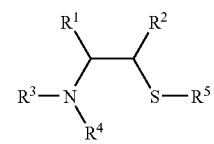

wherein $R^1$ is aryl or alkyl of C1-C9;
$R^2$ is aryl or alkyl of C1-C9;
$R^3$ is aryl or alkyl of C1-C9;
$R^4$ is aryl or alkyl of C1-C9; or
$R^3$, $R^4$ and N form a three-to-eight-membered heterocycle;
with the proviso that $R^3$, $R^4$ and N form pyrrolidinyl or morpholinyl as $R^1$ and $R^2$ are both phenyl; and
$R^5$ is H or alkyl of C1-C6.

[Preparation Mode]

In general, the aminothiol compounds can be prepared through procedures shown in Scheme A.

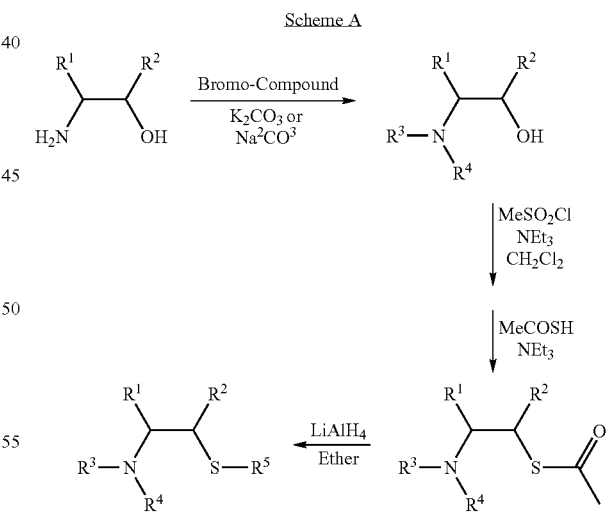

Scheme A includes steps of: (a) reacting amino-alcohol with bromo-compound and carbonate of alkaline metal to form the specific ligand of $R^3$, $R^4$ and N; (b) replacing —OH with —SAc by adding MeSO$_2$Cl and NEt$_3$ (c) adding LiAlH$_4$ to form —SH.

The following EXAMPLEs indicate procedures for preparing representative aminothiol compounds of the present invention. Table 1 lists codes of different ligands shown in the compound of formula (I), so that the aminothiol compounds of the present invention can be simply represented with combinations of such codes.

TABLE 1

| R¹ | | R² | | N-R³-R⁴ | | R⁵ | |
|---|---|---|---|---|---|---|---|
| code | ligand | code | ligand | code | ligand | code | ligand |
| 2 | methyl | b | methyl | 2 | Buⁿ (n-butyl) | c | H |
| 3 | Buⁿ (n-butyl) | c | Buⁿ (n-butyl) | 3 | Bn (benzyl) | | |
| 4 | i-butyl | f | i-propyl | 4 | pyrrolidinyl | | |
| 5 | Bn (benzyl) | g | Ph (phenyl) | 5 | piperidyl | | |
| 6 | i-propyl | | | 6 | morpholinyl | | |
| 7 | Ph (phenyl) | | | | | | |

For example, compound (2b4c) is an aminothiol compound of the present invention, wherein R¹ is methyl; R² is methyl; N, R³ and R⁴ form a five-membered heterocycle, pyrrolidinyl; and R⁵ is H. As for the middle product obtained in step (a), the last code "a" represents the alcohol ligand, —OH.

EXAMPLES 1 AND 2

Preparation of (2R,3S)-4-Methyl-3-(1-pyrrolidinyl) pentane-2-thiol (6b4c) and (3R,4S)-2-Methyl-4-(1-pyrrolidinyl)pentane-3-thiol (2f4c)

Step (a): Preparing (2R,3S)-4-Methyl-3-(1-pyrrolidinyl)pentan-2-ol (6b4a)

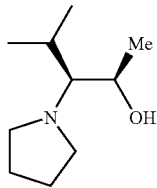

To a three-necked flask, (2R,3S)-3-amino-4-methylpentan-2-ol (0.585 g, 5.0 mmol), Na₂CO₃ (1.16 g, 11.0 mmol) and CH₃CN (20 mL) are added under the nitrogen system and then heated with refluxing. Next, Br₂C₄H₈ (1.295 g, 6.0 mmol) is injected into the solution. After complete reaction for 12 hours, H₂O (20 mL) is added to terminate the reaction. The product is repeatedly extracted with EtOAc (20 mL), wherein the organic phase is dehydrated with Na₂SO₄. A coarse product is obtained after filtration and concentration. Column chromatography (Silica gel 50 g, eluent is n-Hexane:EtOAc=1:1) is used to purify the coarse product and a slightly-yellow liquid (0.85 g) is obtained. The yield is 85% and the other analysis includes:

¹H NMR (400 MHz, CDCl₃)

δ 0.87 (d, J=6.4 Hz, 3H, CH(CH₃)₂), 0.96 (d, J=6.4 Hz, 3H, CH(CH₃)₂), 1.05 (d, J=6.4 Hz, 3H, CHOHCH₃), 1.72–1.79 (m, 4H, —(CH₂)₂—), 1.82–2.00 (m, 1H, CH(CH₃)₂), 2.48 (dd, J₁=4.8 Hz, J₂=10.0 Hz, 1H, NCH), 2.80–2.92 (m, 4H, NCH₂—), 3.70–3.80 (m, 1H, CHOH)

¹³C NMR (100 MHz, CDCl₃)

δ 18.59 (CHOHCH₃), 19.80 (CH(CH₃)₂), 21.38 (CH(CH₃)₂), 23.93 (—CH₂—) 27.30 (CH(CH₃)₂), 50.91 (NCH₂—), 65.64 (NCH), 69.50 (CHOH)

Element analysis: C₁₀H₂₁NO
theoretical: C, 70.12; H, 12.36; N, 8.18
experimental: C, 71.16; H, 12.28; N, 8.14

High-resolution MS (70 eV) m/e theoretical: 171.1623
experimental: 172.1699

[α]²⁵_D=+42.1 (c=1.45, CDCl₃)

Step (b): Preparing (2R,3S)-4-Methyl-3-(1-pyrrolidinyl)-2-thioacetylpentane (6b4b)

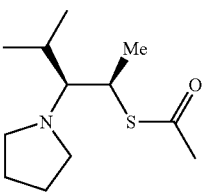

and (3R,4S)-2-Methyl-4-(1-pyrrolidinyl)-3-thioacetylpentane (2f4b)

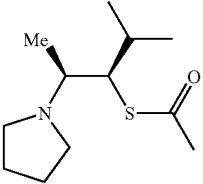

To a three-necked flask, compound (6b4a) (0.855 g, 5.0 mmol), CH₂Cl₂ (20 mL) and NEt₃ (1.01 g, 10.0 mmol) are added under nitrogen system. Next, MeSO₂Cl (0.69 g, 6.0 mmol, dissolved in 20 mL CH₂Cl₂) is added dropwisely at 0° C. After complete reaction for 2 hours, a coarse product is obtained through repeated depressing concentration and adding benzene therein. The coarse product is then added into benzene (20 mL) with refluxing, and MeCOSH (0.46 g, 6.0 mmol) and NEt₃ (1.01 g, 10.0 mmol) dissolved in 20 mL benzene are injected into the above solution under the nitrogen system. After 12 hours, H₂O (20 mL) is added to terminate the reaction. The product is repeatedly extracted with EtOAc (20 mL), wherein the organic phase is dehydrated with Na₂SO₄. A coarse product is obtained after filtration and concentration. Column chromatography (Silica gel 70 g, eluent is n-Hexane:NEt₃=100:1) is used to purify the coarse product and two orange liquids, compound (6b4b) (0.229 g) and compound (2f4b) (0.458 g), are obtained. The yields of compound (6b4b) and compound (2f4b) are 20% and 40%, respectively. The other analysis for compound (6b4b) includes:

¹H NMR (400 MHz, CDCl₃)

δ 0.92 (d, J=7.2 Hz, 3H, CH(CH₃)₂), 0.94 (d, J=7.2 Hz, 3H, CH(CH₃)₂), 1.27 (d, J=6.8 Hz, 3H, SCHCH₃), 1.66-1.73 (m, 4H, —(CH₂)₂—), 1.90-2.05 (m, 1H, CH(CH₃)₂), 2.27 (s, 3H, SCOCH₃), 2.41 (dd, J₁=3.2 Hz, J₂=8.0 Hz, 1H, NCH), 2.67-2.74 (m, 2H, NCH₂—), 2.75-2.81 (m, 2H, NCH₂—), 3.86-4.05 (m, 1H, SCH)

¹³C NMR (100 MHz, CDCl₃)

δ 18.38 (SCHCH₃) 20.37 (CH(CH₃)₂), 21.18 (CH(CH₃)₂), 24.20 (—CH₂—), 29.40 (CH(CH₃)₂), 30.66 (SCOCH₃), 43.29 (NCH) 51.06 (NCH₂—), 69.61 (SCHCH₃), 196.77 (SCOCH₃)

Element analysis C₁₂H₂₃NOS theoretical: C, 62.83; H, 10.11; N, 6.11 experimental: C, 62.90; H, 10.10; N, 6.02

High-resolution MS (70 eV) m/e theoretical: 229.1500 experimental: 229.1523

[α]25D=+48.1° (c=1.05, CDCl₃)

The other analysis for compound (2f4b) includes:

¹H NMR (400 MHz, CDCl₃)

δ 0.91 (d, J=6.8 Hz, 3H, CH(CH₃)₂), 0.96 (d, J=7.2 Hz, 3H, CH(CH₃)₂), 1.03 (d, J=6.8 Hz, 3H, NCHCH₃), 1.68-1.73 (m, 4H, —(CH₂)₂—), 1.86-2.11 (m, 1H, CH(CH₃)₂), 2.33 (s, 3H, SCOCH₃), 2.42-2.64 (m, 4H, NCH₂—), 2.42-2.64 (m, 1H, NCH), 3.60 (dd, J₁=4.8 Hz, J₂=8.0 Hz, 1H, SCH),

¹³C NMR (100 MHz, CDCl₃)

δ 13.78 (NCHCH₃) 19.81 (CH(CH₃)₂), 20.78 (CH(CH₃)₂), 23.26 (—CH₂—), 30.25 (CH(CH₃)₂), 30.72 (SCOCH₃), 50.64 (NCH₂—), 54.84 (NCH), 58.89 (SCHCH₃), 195.56 (SCOCH₃)

Element analysis C₁₂H₂₃NOS theoretical: C, 62.83; H, 10.11; N, 6.11 experimental: C, 62.56; H, 10.25; N, 5.97

High-resolution MS (70 eV) m/e theoretical: 299.1500 experimental: 299.1508

[α]25D=+41.7° (c=0.99, CDCl₃)

Step (c): Preparing (2R,3S)-4-Methyl-3-(1-pyrrolidinyl)pentane-2-thiol (6b4c)

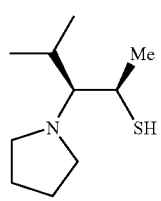

and (3R,4S)-2-Methyl-4-(1-pyrrolidinyl)pentane-3-thiol (2f4c)

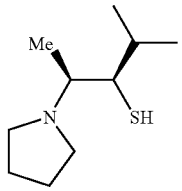

To a three-necked flask, LAH (LiAlH₄, 0.076 g, 2.0 mmol) and ether (10 mL) are added under nitrogen system. Next, compound (6b4b) (0.229 g, 1.0 mmol) or compound (2f4b) (0.229 g, 1.0 mmol) dissolved in 10 mL ether is slowly added into the flask within 30 min at 0° C. After reaction for 1 hour, 15% NaOH is added to the flask until a white solid is present complete. The solid is filtered and repeatedly washed with a solvent. The filtrate is then concentrated to obtain a coarse product. Column chromatography (Silica gel 40 g, eluent is n-Hexane:NEt₃=100:1) is used to purify the coarse product and two orange liquids, compound (6b4c) (0.15 g) and compound (2f4c) (0.15 g), are obtained. The yields of compound (6b4c) and compound (2f4b) are 80% and 80%, respectively. The other analysis for compound (6b4c) includes:

¹H NMR (400 MHz, CDCl₃)

δ 0.88 (d, J=6.8 Hz, 3H, CH(CH₃)₂), 0.93 (d, J=6.4 Hz, 3H, CH(CH₃)₂), 1.35 (d, J=6.8 Hz, 3H, CHSHCH₃), 1.65-1.73 (m, 4H, —(CH₂)₂—), 1.98-2.10 (m, 1H, CH(CH₃)₂), 2.55 (dd, J₁=3.6 Hz, J₂=7.2 Hz, 1H, NCH), 2.70-2.75 (m, 2H, NCH₂—), 2.76-2.82 (m, 2H, NCH₂—), 3.03-3.20 (m, 1H, CHOH)

¹³C NMR (100 MHz, CDCl₃)

δ 20.75 (CH(CH₃)₂), 21.24 (CHSHCH₃), 22.26 (CH(CH₃)₂), 24.49 (—CH₂—) 29.17 (CH(CH₃)₂), 38.44 (NCH), 51.18 (NCH₂—), 70.87 (SCH)

Element analysis C₁₀H₂₁NS theoretical: C, 64.11; H, 11.30; N, 7.48 experimental: C, 64.35; H, 11.12; N, 7.65

High-resolution MS (70 eV) m/e theoretical: 187.1395 experimental: 187.1366

[α]25D=+17.4° (c=0.83, CDCl₃)

The other analysis for compound (2f4c) includes:

¹H NMR (400 MHz, CDCl₃)

δ 0.92 (d, J=6.8 Hz, 3H, CH(CH₃)₂), 1.01 (d, J=6.4 Hz, 3H, CH(CH₃)₂), 1.04 (d, J=6.4 Hz, 3H, NCHCH₃), 1.69-1.75 (m, 4H, —(CH₂)₂—), 1.69-1.75 (m, 1H, CH(CH₃)₂), 2.35-2.41 (m, 1H, NCH), 2.43-2.49 (m, 2H, NCH₂—), 2.52-2.58 (m, 2H, NCH₂—), 2.84 (dd, J₁=4.0 Hz, J₂=9.6 Hz, 1H, SHCH)

¹³C NMR (100 MHz, CDCl₃)

δ 12.08 (NCHCH₃), 20.47 (CH(CH₃)₂), 21.71 (CH(CH₃)₂), 23.27 (—CH₂—) 31.24 (CH(CH₃)₂), 50.95 (NCH₂—), 52.17 (NCH), 60.54 (SCH)

Element analysis C₁₀H₂₁NS theoretical: C, 64.11; H, 11.30; N, 7.48 experimental: C, 63.98; H, 11.25; N, 7.45

High-resolution MS (70 eV) m/e theoretical: 187.1395 experimental: 187.1386

[α]25D=+23.7° (c=1.51, CDCl₃)

EXAMPLES 3 AND 4

Preparation of (3S,4R)-2-Methyl-3-(1-pyrrolidinyl)octane-4-thiol (6c4c) and (3R,4S)-2-Methyl-4-(1-pyrrolidinyl)octane-3-thiol (3f4c)

Step (a): Preparing (3S,4R)-2-Methyl-3-(1-pyrrolidinyl)octan-4-ol (6c4a)

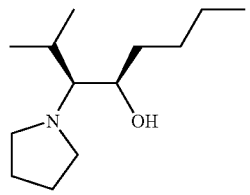

Repeat Step (a) of EXAMPLE 1, but (2R,3S)-3-amino-4-methyl pentan-2-ol is replaced with (3S,4R)-3-amino-2-methyloctan-4-ol. The analysis for compound (6c4a) includes:

$^1$H NMR(400 MHz, CDCl$_3$)

δ 0.77-0.92 (m, 3H, (CH$_2$)$_3$CH$_3$), 0.77-0.92 (m, 6H, CH(CH$_3$)$_2$), 1.06-1.62 (m, 6H, (CH$_2$)$_3$CH$_3$), 1.62-1.81 (m, 4H, —(CH$_2$)$_2$—), 1.89-2.05 (m, 1H, CH(CH$_3$)$_2$), 2.47 (dd, J$_1$=4.8 Hz, J$_2$=9.6 Hz, 1H, NCH), 2.74-2.86 (m, 4H, NCH$_2$—), 3.45-3.52 (m, 1H, CHOH), $^{13}$C NMR(100 MHz, CDCl$_3$)

δ 13.99 (CH$_2$CH$_2$CH$_2$CH$_3$), 20.20 (CH(CH$_3$)$_2$), 21.81 (CH(CH$_3$)$_2$), 22.66 (CH$_2$CH$_2$CH$_2$CH$_3$), 24.23 (—CH$_2$—), 27.48 (CH(CH$_3$)$_2$), 29.23 (CH$_2$CH$_2$CH$_2$CH$_3$), 32.21 (CH$_2$CH$_2$CH$_2$CH$_3$), 50.85 (NCH$_2$—), 69.11 (NCH), 70.58 (CHOH)

Element analysis C$_{13}$H$_{27}$NO theoretical: C, 73.18; H, 12.76; N, 6.56 experimental: C, 73.20; H, 12.63; N, 6.51

High-resolution MS (70 eV) m/e theoretical: 213.2093 experimental: 214.2165

[α]25D=+53.3° (c=1.03, CDCl$_3$)

Step (b): Preparing (3S,4R)-2-Methyl-3-(1-pyrrolidinyl)-4-thioacetyloctane (6c4b)

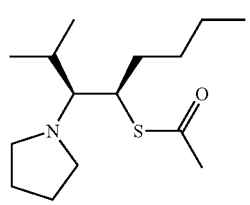

and (3R,4S)-2-Methyl-4-(1-pyrrolidinyl)-3-thioacetyloctane (3f4b)

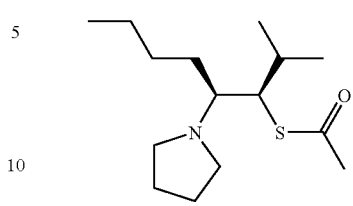

Repeat Step (b) of EXAMPLE 1, but replace compound (6b4a) with compounds (6c4a) or (3f4a). Analysis for product (6c4b) includes:

$^1$H NMR (400 MHz, CDCl$_3$)

δ 0.85 (t, J=7.2 Hz, 3H, (CH$_2$)$_3$CH$_3$), 0.86 (d, J=5.6 Hz, 3H, CH(CH$_3$)$_2$), 0.95 (d, J=5.6 Hz, 3H, CH(CH$_3$)$_2$), 1.20-1.50 (m, 6H, (CH$_2$)$_3$CH$_3$), 1.64-1.72 (m, 4H, —(CH$_2$)$_2$—), 1.85-2.12 (m, 1H, CH(CH$_3$)$_2$), 2.28 (s, 3H, SCOCH$_3$), 2.43 (dd, J$_1$=2.8 Hz, J$_2$=8.0 Hz, 1H, NCH), 2.58-2.66 (m, 2H, NCH$_2$—), 2.68-2.77 (m, 2H, NCH$_2$—), 3.80-3.88 (m, 1H, SCH), $^{13}$C NMR (100 MHz, CDCl$_3$)

δ 14.00 (CH$_2$CH$_2$CH$_2$CH$_3$), 20.50 (CH(CH$_3$)$_2$), 21.19 (CH(CH$_3$)$_2$), 22.56 (CH$_2$CH$_2$CH$_2$CH$_3$), 23.99 (—CH$_2$—), 29.54 (CH(CH$_3$)$_2$), 29.58 (CH$_2$CH$_2$CH$_2$CH$_3$), 30.53 (SCOCH$_3$), 32.16 (CH$_2$CH$_2$CH$_2$CH$_3$), 47.53 (NCH), 50.79 (NCH$_2$—), 70.19 (SCH), 196.26 (SCOCH$_3$)

Element analysis C$_{15}$H$_{29}$NOS theoretical: C, 66.37; H, 10.77; N, 5.16 experimental: C, 66.14; H, 10.85; N, 5.22

High-resolution MS (70 eV) m/e theoretical: 271.1970 experimental: 271.1971

[α]25D=+39.6° (c=1.03, CDCl$_3$)

Analysis for product (3f4b) includes:

$^1$H NMR(400 MHz, CDCl$_3$)

δ 0.82-0.90 (m, 3H, (CH$_2$)$_3$CH$_3$), 0.82-0.90 (m, 3H, CH(CH$_3$)$_2$), 0.93 (d, J=6.4 Hz, 3H, CH(CH$_3$)$_2$), 1.20-1.60 (m, 6H, (CH$_2$)$_3$CH$_3$), 1.65-1.73 (m, 4H, —(CH$_2$)$_2$—), 1.91-2.05 (m, 1H, CH(CH$_3$)$_2$), 2.31 (s, 3H, SCOCH$_3$), 2.50-2.63 (m, 4H, NCH$_2$—), 2.50-2.63 (m, 1H, NCH), 3.63 (t, J=6.0 Hz, 1H, SCH), $^{13}$C NMR (100 MHz, CDCl$_3$)

δ 13.91 (CH$_2$CH$_2$CH$_2$CH$_3$), 19.07 (CH(CH$_3$)$_2$), 20.83 (CH(CH$_3$)$_2$), 22.98 (CH$_2$CH$_2$CH$_2$CH$_3$), 23.56 (—CH$_2$—), 30.26 (CH(CH$_3$)$_2$), 30.49 (CH$_2$CH$_2$CH$_2$CH$_3$), 30.70 (SCOCH$_3$), 30.79 (CH$_2$CH$_2$CH$_2$CH$_3$), 49.33 (NCH$_2$—), 53.70 (NCH), 61.89 (SCH), 195.68 (SCOCH$_3$)

Element analysis C$_{15}$H$_{29}$NOS theoretical: C, 66.37; H, 10.77; N, 5.16 experimental: C, 66.23; H, 10.71; N, 5.02

High-resolution MS (70 eV) m/e theoretical: 271.1970 experimental: 271.1991

[α]25D=+48.2° (c=1.24, CDCl$_3$)

Step (c): Preparing (3S,4R)-2-Methyl-3-(1-pyrrolidinyl)octane-4-thiol (6c4c)

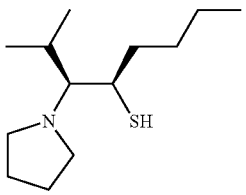

and (3R,4S)-2-Methyl-4-(1-pyrrolidinyl) octane-3-thiol (3f4c)

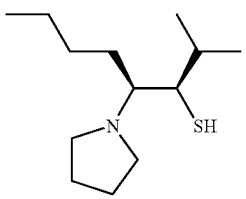

Repeat Step (c) of EXAMPLE 1, but replace compound (6b4b) with compounds (6c4b) or (3f4b). Analysis for product (6c4c) includes:

$^1$H NMR (400 MHz, CDCl$_3$)
  δ 0.84-1.00 (m, 6H, CH(CH$_3$)$_2$), 0.84-1.00 (m, 3H, (CH$_2$)$_3$ CH$_3$), 1.16-1.35 (m, 4H, CH$_2$(CH$_2$)$_2$CH$_3$), 1.48-1.78 (m, 2H, CH$_2$(CH$_2$)$_2$CH$_3$), 1.48-1.78 (m, 4H, —(CH$_2$)$_2$—), 2.00-2.13 (m, 1H, CH(CH$_3$)$_2$), 2.43 (dd, J$_1$=3.6 Hz, J$_2$=8.4 Hz, 1H, NCH), 2.71-2.93 (m, 4H, NCH$_2$—), 2.71-2.963 (m, 1H, SHCH), $^{13}$C NMR (100 MHz, CDCl$_3$)
  δ 14.07 (CH$_2$CH$_2$CH$_2$CH$_3$), 20.88 (CH(CH$_3$)$_2$), 21.39 (CH(CH$_3$)$_2$), 22.49 (CH$_2$CH$_2$CH$_2$CH$_3$), 24.39 (—CH$_2$—), 28.90 (CH(CH$_3$)$_2$), 30.54 (CH$_2$CH$_2$CH$_2$CH$_3$), 34.56 (CH$_2$CH$_2$CH$_2$CH$_3$), 44.95 (NCH), 51.01 (NCH$_2$—), 70.85 (CHSH)

Element analysis C$_{13}$H$_{27}$NS
  theoretical: C, 68.06; H, 11.86; N, 6.11
  experimental: C, 68.21; H, 11.55; N, 6.35

High-resolution MS (70 eV) m/e theoretical: 229.1864
  experimental: 229.1857

[α]25D=+54.3° (c=10.01, CDCl$_3$)

Analysis for product (3f4c) includes:

$^1$H NMR (400 MHz, CDCl$_3$)
  δ 0.86-1.00 (m, 3H, (CH$_2$)$_3$CH$_3$), 0.86-1.00 (m, 6H, CH(CH$_3$)$_2$), 1.23-1.50 (m, 4H, CH$_2$(CH$_2$)$_2$CH$_3$), 1.52-1.73 (m, 2H, CH$_2$(CH$_2$)$_2$CH$_3$), 1.52-1.73 (m, 4H, —(CH$_2$)$_2$—), 1.75-1.92 (m, 1H, CH(CH$_3$)$_2$), 2.33 (dd, J$_1$=4.4 Hz, J$_2$=8.0 Hz, 1H, NCH), 2.47-2.62 (m, 4H, NCH$_2$—), 2.85 (dd, J$_1$=4.4 Hz, J$_2$=8.0 Hz, 1H, SHCH), $^{13}$C NMR (100 MHz, CDCl$_3$)
  δ 13.92 (CH$_2$CH$_2$CH$_2$CH$_3$), 20.13 (CH(CH$_3$)$_2$), 21.23 (CH(CH$_3$)$_2$), 23.21 (CH$_2$CH$_2$CH$_2$CH$_3$), 23.43 (—CH$_2$—), 29.30 (CH$_2$CH$_2$CH$_2$CH$_3$), 30.65 (CH (CH$_3$)$_2$), 31.42 (CH$_2$CH$_2$CH$_2$CH$_3$), 50.24 (NCH$_2$—), 51.99 (NCH), 64.56 (CHSH)

Element analysis C$_{13}$H$_{27}$NS
  theoretical: C, 68.06; H, 11.86; N, 6.11
  experimental: C, 68.21; H, 11.56; N, 6.01

High-resolution MS (70 eV) m/e theoretical: 229.1864
  experimental: 229.1857

[α]25D=+38.8° (c=0.99, CDCl$_3$)

EXAMPLE 5

Preparation of (3R,4S)-2,5-Dimethyl-4-(1-pyrrolidinyl)hexane-3-thiol (6f4c)

Step (a): Preparing (3R,4S)-2,5-Dimethyl-4-(1-pyrrolidinyl)hexan-3-ol (6f4a)

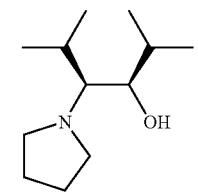

Repeat Step (a) of EXAMPLE 1, but replace (2R,3S)-3-amino-4-methylpentan-2-ol with (3R,4S)-4-amino-2,5-dimethylhexan-3-ol. Analysis for compound (6f4a) includes:

$^1$H NMR (400 MHz, CDCl$_3$)
  δ 0.83 (d, J=6.8 Hz, 3H, NCHCH(CH$_3$)$_2$), 0.97 (d, J=6.8 Hz, 3H, NCHCH(CH$_3$)$_2$), 1.02 (d, J=1.2 Hz, 3H, CHOHCH(CH$_3$)$_2$), 1.04 (d, J=1.2 Hz, 3H, CHOHCH (CH$_3$)$_2$), 1.63-1.73 (m, 4H, —(CH$_2$)$_2$—), 1.74-1.83 (m, 1H, NCHCH(CH$_3$)$_2$), 2.05-2.12 (m, 1H, CHOHCH (CH$_3$)$_2$), 2.21 (dd, J$_1$=3.2 Hz, J$_2$=4.0 Hz, 1H, NCH), 2.55-2.63 (m, 2H, NCH$_2$—), 2.65-2.72 (m, 2H, NCH$_2$—), 3.41 (dd, J$_1$=4.4 Hz, J$_2$=9.2 Hz, 1H, CHOH)

$^{13}$C NMR (100 MHz, CDCl$_3$)
  δ 19.20 (NCHCH(CH$_3$)$_2$), 19.30 (NCHCH(CH$_3$)$_2$), 19.62 (CHOHCH(CH$_3$)$_2$), 22.68 (CHOHCH(CH$_3$)$_2$), 23.40 (—CH$_2$—) 26.99 (NCHCH(CH$_3$)$_2$), 30.59 (CHOHCH (CH$_3$)$_2$), 51.59 (NCH$_2$—), 68.34 (NCH), 77.60 (CHOH)

Element analysis C$_{12}$H$_{25}$NO
  theoretical: C, 72.31; H, 12.64; N, 7.03
  experimental: C, 72.18; H, 12.73; N, 6.89

High-resolution MS (70 eV) m/e theoretical: 199.1936
  experimental: 200.2011

[α]25D=+45.7° (c=1.21, CDCl$_3$)

Step (b): Preparing (3R,4S)-2,5-Dimethyl-4-(1-pyrrolidinyl)-3-thioacetylhexane (6f4b)

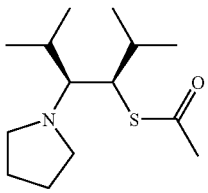

Repeat Step (b) of EXAMPLE 1, but replace compound (6b4a) with compound (6f4a). Analysis for product (6f4b) includes:

¹H NMR (400 MHz, CDCl₃)
δ 0.88 (d, J=6.8 Hz, 3H, NCHCH(CH₃)₂), 0.90-0.98 (m, 3H, NCHCH(CH₃)₂), 0.90-0.98 (m, 6H, SCHCH(CH₃)₂), 1.66-1.71 (m, 4H, —(CH₂)₂—), 1.88-2.00 (m, 1H, NCHCH(CH₃)₂), 2.01-2.12 (m, 1H, SCHCH(CH₃)₂), 2.34 (s, 3H, SCOCH₃), 2.62-2.70 (m, 2H, NCH₂—), 2.71-2.77 (m, 2H, NCH₂—), 2.62-2.77 (m, 1H, NCH), 3.79 (dd, J₁=5.2 Hz, J₂=6.4 Hz, 1H, SCH)

¹³C NMR (100 MHz, CDCl₃)
δ 18.62 (NCHCH(CH₃)₂), 19.99 (NCHCH(CH₃)₂), 21.10 (SCHCH(CH₃)₂), 21.59 (SCHCH(CH₃)₂), 24.01 (—CH₂—), 30.44 (NCHCH(CH₃)₂), 30.54 (SCHCH(CH₃)₂), 30.70 (SCOCH₃), 49.24 (NCH₂—), 50.80 (NCH), 64.73 (SCH), 195.37 (SCOCH₃)

Element analysis C₁₄H₂₇NOS
theoretical: C, 65.32; H, 10.57; N, 5.44
experimental: C, 65.20; H, 10.81; N, 5.14

High-resolution MS (70 eV) m/e theoretical: 257.1813
experimental: 257.1859

[α]25D=+53.9° (c=1.23, CDCl₃)

Step (c): Preparing (3R,4S)-2,5-Dimethyl-4-(1-pyrrolidinyl)hexane-3-thiol (6f4c)

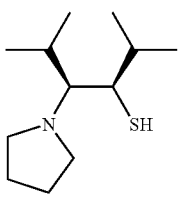

Repeat Step (c) of EXAMPLE 1, but replace compound (6b4b) with compound (6f4b). Analysis for product (6f4c) includes:

¹H NMR (400 MHz, CDCl₃)
δ 0.89 (d, J=6.4 Hz, 3H, NCHCH(CH₃)₂), 0.92-1.06 (m, 3H, NCHCH(CH₃)₂), 0.92-1.06 (m, 6H, SHCHCH(CH₃)₂), 1.62-1.72 (m, 4H, —(CH₂)₂—), 1.89-1.95 (m, 1H, NCHCH(CH₃)₂), 2.13-2.25 (m, 1H, SHCHCH(CH₃)₂), 2.52 (dd, J₁=4.4 Hz, J₂=8.0 Hz, 1H, NCH), 2.64-2.73 (m, 4H, NCH₂—), 2.92 (dd, J₁=4.4 Hz, J₂=7.6 Hz, 1H, CHSH)

¹³C NMR (100 MHz, CDCl₃)
δ 17.63 (NCHCH(CH₃)₂), 19.56 (NCHCH(CH₃)₂), 21.57 (CHSHCH(CH₃)₂), 21.79 (CHSHCH(CH₃)₂), 24.14 (—CH₂—) 29.40 (NCHCH(CH₃)₂), 29.69 (CHSHCH(CH₃)₂), 48.77 (NCH), 50.03 (NCH₂—), 66.19 (CHSH)

Element analysis C₁₂H₂₅NS
theoretical: C, 66.91; H, 11.70; N, 6.50
experimental: C, 66.38; H, 10.91; N, 6.28

High-resolution MS (70 eV) m/e theoretical: 215.1708
experimental: 215.1712

[α]25D=+13.7° (c=0.99, CDCl₃)

EXAMPLE 6

Preparation of (1R,2S)-3-Methyl-1-phenyl-2-(1-pyrrolidinyl)butane-1-thiol (6g4c)

Step (a): Preparing (1R,2S)-3-Methyl-1-phenyl-2-(1-pyrrolidinyl)butan-1-ol (6g4a)

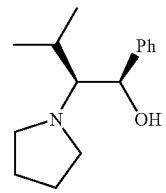

Repeat Step (a) of EXAMPLE 1, but replace (2R,3S)-3-amino-4-methylpentan-2-ol with (1R,2S)-2-amino-3-methyl-1-phenylbutan-1-ol, and replace Na₂CO₃ (1.16 g, 11.0 mmol) with K₂CO₃ (1.52 g, 11.0 mmol). Column chromatography (Silica gel, eluent is n-Hexane:EtOAc=10:1) is used to purify the coarse product and a slightly-yellow liquid (1.00 g) is obtained. The yield is 86% and the other analysis includes:

¹H NMR (400 MHz, CDCl₃)
δ 0.80 (d, J=6.8 Hz, 3H, CH(CH₃)₂), 0.96 (d, J=6.8 Hz, 3H, CH(CH₃)₂), 1.62-1.70 (m, 4H, —(CH₂)₂—), 1.72-1.82 (m, 1H, CH(CH₃)₂), 2.54 (dd, J₁=4.4 Hz, J₂=8.0 Hz, 1H, NCH), 2.57-2.64 (m, 2H, NCH₂—), 2.68-2.74 (m, 2H, NCH₂—), 4.92 (d, J=4.0 Hz, 1H, CHOH), 7.14-7.34 (m, 5H, ArH)

¹³C NMR (100 MHz, CDCl₃)
δ 20.28 (CH(CH₃)₂), 21.81 (CH(CH₃)₂), 23.78 (—CH₂—), 27.88 (CH(CH₃)₂), 51.47 (NCH₂—), 72.29 (NCH), 72.51 (CHOH), 126.08, 126.62, 127.79, 142.88 (Ph)

Element analysis C₁₅H₂₃NO
theoretical: C, 77.21; H, 9.93; N, 6.00
experimental: C, 77.11; H, 9.73; N, 6.23

High-resolution MS (70 eV) m/e theoretical: 233.1780
experimental: 234.1865

[α]25D=−41.3° (c=1.38, CDCl₃)

Step (b): Preparing (1R,2S)-3-Methyl-1-phenyl-2-(1-pyrrolidinyl)-1-thioacetyl butane (6g4b)

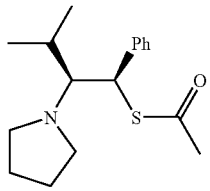

Repeat Step (b) of EXAMPLE 1, but replace compound (6b4a) with compound (6g4a). Column chromatography (Silica gel, eluent is n-Hexane:NEt$_3$=100:1) is used to purify the coarse product and a slightly-yellow liquid (1.09 g) is obtained. The yield is 75% and the other analysis includes:

$^1$H NMR (400 MHz, CDCl$_3$)
δ 0.90 (d, J=6.8 Hz, 3H, CH(CH$_3$)$_2$), 0.99 (d, J=6.4 Hz, 3H, CH(CH$_3$)$_2$), 1.45-1.55 (m, 4H, —(CH$_2$)$_2$—), 1.92-2.04 (m, 1H, CH(CH$_3$)$_2$), 2.26 (s, 3H, SCOCH$_3$), 2.60-2.69 (m, 4H, NCH$_2$—), 2.97 (t, J=6.4 Hz, 1H, NCH), 4.99 (d, J=6.4 Hz, 1H, SCH), 7.14-7.41 (m, 5H, ArH)

$^{13}$C NMR (100 MHz, CDCl$_3$)
δ 19.82 (CH(CH$_3$)$_2$), 21.62 (CH(CH$_3$)$_2$), 24.31 (—CH$_2$—), 30.57 (CH(CH$_3$)$_2$), 30.59 (SCOCH$_3$), 49.69 (NCH), 50.42 (NCH$_2$—), 69.33 (SCH), 126.73, 127.86, 128.70, 141.80 (Ph), 194.60 (SCOCH$_3$)

Element analysis C$_{17}$H$_{25}$NOS
theoretical: C, 70.06; H, 8.65; N, 4.81
experimental: C, 69.68; H, 8.80; N, 4.63

High-resolution MS (70 eV) m/e theoretical: 291.1657
experimental: 291.1661

[α]25D=−240.8° (c=1.02, CDCl$_3$)

Step (c): Preparing (1 R,2S)-3-Methyl-1-phenyl-2-(1-pyrrolidinyl)butane-1-thiol (6g4c)

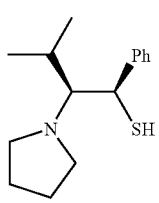

Repeat Step (c) of EXAMPLE 1, but replace compound (6b4b) with compound (6g4b). A slightly-yellow liquid (0.401 g) is obtained through pumping concentration. The yield is 85% and other analysis includes:

$^1$H NMR (400 MHz, CDCl$_3$)
δ 0.95 (d, J=7.2 Hz, 3H, CH(CH$_3$)$_2$), 0.99 (d, J=6.4 Hz, 3H, CH(CH$_3$)$_2$), 1.37-1.48 (m, 4H, —(CH$_2$)$_2$—), 2.06-2.15 (m, 1H, CH(CH$_3$)$_2$), 2.54-2.70 (m, 4H, NCH$_2$—), 3.00 (dd, J$_1$=5.2 Hz, J$_2$=7.6 Hz, 1H, NCH), 4.30 (d, J=7.6 Hz, 1H, SHCH), 7.12-7.40 (m, 5H, ArH)

$^{13}$C NMR(100 MHz, CDCl$_3$)
δ 18.95 (CH(CH$_3$)$_2$), 21.67 (CH(CH$_3$)$_2$), 24.46 (—CH$_2$—), 30.42 (CH(CH$_3$)$_2$), 50.60 (NCH$_2$—), 70.03 (NCH), 77.20 (CHSH), 126.73, 127.9, 128.1, 144.57 (Ph)

Element analysis C$_{15}$H$_{23}$NS
theoretical: C, 72.23; H, 9.29; N, 5.62
experimental: C, 72.01; H, 9.88; N, 5.32

High-resolution MS (70 eV) m/e theoretical: 249.1551
experimental: 249.1554

[α]25D=−489.0° (c=1.01, CDCl$_3$)

EXAMPLE 7

Preparation of (1R,2S)-1,2-Diphenyl-2-piperidin-1-yl-ethanethiol (6g5c)

Step (a): Preparing (6g5a)

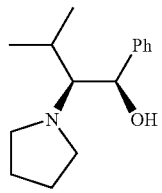

Repeat Step (a) of EXAMPLE 6, but replace 1,4-dibromobutane with 1,5-dibromopentane. Column chromatography (Silica gel, eluent is n-Hexane:EtOAc=10:1) is used to purify the coarse product and a slightly-yellow liquid (1.00 g) is obtained. The yield is 86% and the other analysis includes:

$^1$H NMR (400 MHz, CDCl$_3$)
δ 0.80 (d, J=6.8 Hz, 3H, CH(CH$_3$)$_2$), 0.96 (d, J=6.8 Hz, 3H, CH(CH$_3$)$_2$), 1.62-1.70 (m, 4H, —(CH$_2$)$_2$—), 1.72-1.82 (m, 1H, CH(CH$_3$)$_2$), 2.54 (dd, J$_1$=4.4 Hz, J$_2$=8.0 Hz, 1H, NCH), 2.57-2.64 (m, 2H, NCH$_2$—), 2.68-2.74 (m, 2H, NCH$_2$—), 4.92 (d, J=4.0 Hz, 1H, CHOH), 7.14-7.34 (m, 5H, ArH)

$^{13}$C NMR (100 MHz, CDCl$_3$)
δ 20.28 (CH(CH$_3$)$_2$), 21.81 (CH(CH$_3$)$_2$), 23.78 (—CH$_2$—), 27.88 (CH(CH$_3$)$_2$), 51.47 (NCH$_2$—), 72.29 (NCH), 72.51 (CHOH), 126.08, 126.62, 127.79, 142.88 (Ph)

Element analysis C$_{18}$H$_{21}$NO
theoretical: C, 77.21; H, 9.93; N, 6.00
experimental: C, 77.11; H, 9.73; N, 6.91

High-resolution MS (70 eV) m/e theoretical:233.1780
experimental: 234.1865

[α]$^{25}$$_D$=−41.3 (c=1.38, CHCl$_3$)

Step (b): Preparing (1R,2S)-Thioavcetic acidS-(3-methyl-1-phenyl-2-pyrrolidin-1-yl-butyl)ester (6g5b)

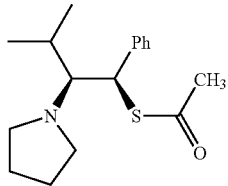

Repeat Step (b) of EXAMPLE 6, but replace compound (6g4a) with compound (6g5a). Column chromatography (Silica gel, eluent is n-Hexane:NEt$_3$=100:1) is used to purify the coarse product and a slightly-yellow liquid (1.09 g) is obtained. The yield is 75% and the other analysis includes:

$^1$H NMR(40 MHz, CDCl$_3$)
δ 0.90 (d, J=6.8 Hz, 3H, CH(C$\underline{H}_3$)$_2$), 0.99 (d, J=6.4 Hz, 3H, CH(C$\underline{H}_3$)$_2$), 1.45-1.55 (m, 4H, —(C$\underline{H}_2$)$_2$—), 1.92-2.04 (m, 1H, C$\underline{H}$(CH$_3$)$_2$), 2.26 (s, 3H, SCOC$\underline{H}_3$), 2.60-2.69 (m, 4H, NCH$_2$—), 2.97 (t, J=6.4 Hz, 1H, NCH), 4.99 (d, J=6.4 Hz, 1H, SCH), 7.14-7.41 (m, 5H, ArH)

$^{13}$C NMR (100 MHz, CDCl$_3$)
δ 19.82 (CH($\underline{C}$H$_3$)$_2$), 21.62 (CH($\underline{C}$H$_3$)$_2$), 24.31 (—CH$_2$—), 30.57 ($\underline{C}$H(CH$_3$)$_2$), 30.59 (SCO$\underline{C}$H$_3$), 49.69 (NCH), 50.42 (NCH$_2$—), 69.33 ($\underline{C}$HSCOCH$_3$), 126.73, 127.86, 128.70, 141.80 (Ph), 194.60 (S$\underline{C}$OCH$_3$)

Element analysis C$_{21}$H$_{25}$NOS
theoretical: C, 70.06; H, 8.65; N, 4.81; S 11.00
experimental: C, 69.68; H, 8.80; N, 4.63; S11.13

High-resolution MS (70 eV) m/e theoretical: 291.1657
experimental: 291.1661

[α]$^{25}_D$=−240.8 (c=1, CHCl$_3$)

Step (c): Preparing (1R,2S)-3-Methyl-1-phenyl-2-pyrrolidin-1-yl-butane-1-thiol (6g5c)

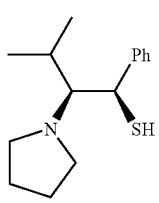

Repeat Step (c) of EXAMPLE 6, but replace compound (6g4b) with compound (6g5b). A slightly-yellow liquid (0.401 g) is obtained. The yield is 85%, and the other analysis includes:

$^1$H NMR (400 MHz, CDCl$_3$)
δ 0.95 (d, J=7.2 Hz, 3H, CH(C$\underline{H}_3$)$_2$), 0.99 (d, J=6.4 Hz, 3H, CH(C$\underline{H}_3$)$_2$), 1.37-1.48 (m, 4H, —(C$\underline{H}_2$)$_2$—), 2.06-2.15 (m, 1H, C$\underline{H}$(CH$_3$)$_2$), 2.54-2.70 (m, 4H, NCH$_2$—), 3.00 (dd, J$_1$=5.2 Hz, J$_2$=7.6 Hz, 1H, NCH), 4.30 (d, J=7.6 Hz, 1H, SHC$\underline{H}$), 7.12-7.40 (m, 5H, ArH)

$^{13}$C NMR (100 MHz, CDCl$_3$)
δ 18.95 (CH($\underline{C}$H$_3$)$_2$), 21.67 (CH($\underline{C}$H$_3$)$_2$), 24.46 (—CH$_2$—), 30.42 ($\underline{C}$H(CH$_3$)$_2$), 50.60 (NCH$_2$—), 70.03 (N$\underline{C}$H), 77.20 ($\underline{C}$HSH), 126.73, 127.9, 128.1, 144.57 (Ph), Element analysis C$_{24}$H$_{33}$NOS
theoretical: C, 72.23; H, 9.29; N, 5.62
experimental: C,72.01; H, 9.88; N, 5.32

High-resolution MS (70 eV) m/e theoretical: 249.1551
experimental: 249.1554

[α]$^{25}_D$=−489.0 (c=1, CHCl$_3$)

EXAMPLE 8

Preparation of (1R,2S)-1,2-Diphenyl-2-piperidin-1-yl-ethanethiol (7g4c)

Step (a): Preparing (1R,2S)-1,2-Diphenyl-2-pyrrolidine-1-yl-ethanol (6g5a)

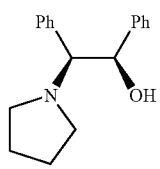

Repeat Step (a) of EXAMPLE 6, but replace (1R,2S)-2-amino-1-phenyl-3-methyl-butanol with (1R,2S)-2-amino-1,2-diphenyl-ethanol. Column chromatography (Silica gel, eluent is n-Hexane:EtOAc=5:1) is used to purify the coarse product and a white solid (1.24 g) is obtained. The yield is 93% and the other analysis includes:

$^1$H NMR(400 MHz, CDCl$_3$)
δ 1.82-1.85 (m, 4H, N(CH$_2$C$\underline{H}_2$)$_2$), 2.59-2.62 (m, 2H, NCH$_2$), 2.74-2.76 (m, 2H, NCH$_2$), 3.30 (d, J=3.2 Hz, 1H, NCH), 5.24 (d, J=3.0 Hz, 1H, C$\underline{H}$OH), 6.97-7.25 (m, 10H, ArH)

$^{13}$C NMR(100 MHz, CDCl$_3$)
δ 23.47 (N(CH$_2$$\underline{C}$H$_2$)$_2$), 52.94 (N($\underline{C}$H$_2$)$_2$), 73.99 (NCH), 77.31 (CHOH), 126.08, 126.70, 127.02, 127.19, 127.42, 129.25, 137.47, 140.69 (2Ph)

Element analysis C$_{18}$H$_{21}$NO
theoretical: C,80.86; H,7.91; N,5.24
experimental: C,81.06; H,7.65; N,5.11

High-resolution MS (70 eV) m/e theoretical: 267.3649
experimental: 267.3688

[α]$^{25}_D$=−87.5 (c=1, CHCl$_3$)

melt point: 113.65±0.45° C.

Step (b): Preparing (1R,2S)-1,2-Diphenyl-2-pyrrolidine-1-yl-1-thioacetyl-ethane (7g4b)

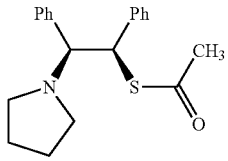

Repeat Step (c) of EXAMPLE 6, but replace compound (6g4b) with compound (7g4a). Column chromatography (Silica gel, eluent is n-Hexane:NEt$_3$=100:1) is used to purify the coarse product and a yellow liquid (1.33 g) is obtained. The yield is 82% and the other analysis includes:

$^1$H NMR (400 MHz, CDCl$_3$)
 δ 1.74-1.78 (m, 4H, N(CH$_2$CH$_2$)$_2$), 2.28 (s, 3H, COCH$_3$), 2.50-2.57 (m, 4H, N(CH$_2$)$_2$), 3.48 (d, J=4.8 Hz, 1H, NCH), 5.25 (d, J=5.2 Hz, 1H, SCH), 6.88-7.26 (m, 10H, ArH)

$^{13}$C NMR (100 MHz, CDCl$_3$)
 δ 23.33 (N(CH$_2$CH$_2$)$_2$), 30.83 (COCH$_3$), 52.62 (N(CH$_2$)$_2$), 52.85 (NCH), 74.99 (SCH), 126.88, 127.48, 127.59, 128.88, 129.00, 138.64, 140.33 (2Ph), 196.58 (SCOCH$_3$)

Element analysis C$_{20}$H$_{23}$NOS
 theoretical: C, 73.81; H, 7.12; N, 4.30
 experimental: C, 73.55; H, 7.26; N, 4.38

High-resolution MS (70 eV) m/e theoretical: 325.4737
 experimental: 325.4245

[α]$^{25}_D$=−32.5 (c=1, CHCl$_3$)

Step (c): Preparing (1R,2S)-1,2-Diphenyl-2-pyrrolidine-1-yl-ethane-1-thiol (7g4c)

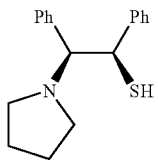

Repeat Step (c) of EXAMPLE 6, but replace compound (6g4b) with compound (7g4b). A slightly-yellow liquid (0.43 g) is obtained. The yield is 76%, and the other analysis includes:

$^1$H NMR (400 MHz, CDCl$_3$)
 δ 1.72-1.79 (m, 4H, N(CH$_2$CH$_2$)$_2$), 2.29(s, 1H, SH), 2.45-2.51 (m, 2H, NCH$_2$), 2.55-2.61 (m, 2H, NCH$_2$), 3.46 (d, J=5.6 Hz, 1H, NCH), 4.70 (d, J=5.2 Hz, 1H, CHSH), 6.96-7.36 (m, 10H, ArH)

$^{13}$C NMR (100 MHz, CDCl$_3$)
 δ 23.47 (N(CH$_2$CH$_2$)$_2$), 48.60 (NCH), 52.30(N(CH$_2$)$_2$), 75.70 (CHSH), 127.05, 127.09, 127.35, 127.72, 128.63, 129.79, 137.40, 140.85 (2Ph)

Element analysis C$_{18}$H$_{21}$NS
 theoretical: C,76.28; H,7.47; N,4.94
 experimental: C,76.06; H,7.28; N,5.23

High-resolution MS (70 eV) m/e theoretical: 283.4369
 experimental: 283.4348

[α]$^{25}_D$=−162.0 (c=1, CHCl$_3$)

EXAMPLE 9

Preparation of (1R,2S)-1,2-Diphenyl-2-piperidin-1-yl-ethanethiol (7g5c)

Step (a): Preparing (1R,2S)-1,2-Diphenyl-2-piperidin-1-yl-ethanol (7g5a)

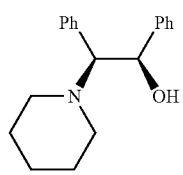

Repeat Step (a) of EXAMPLE 6, but replace (1R,2S)-2-amino-1-phenyl-3-methyl-butanol with (1R,2S)-2-amino-1,2-diphenyl-ethanol, and replace 1,4-dibromobutane with 1,5-dibromopentane. Column chromatography (Silica gel 50 g, eluent is n-Hexane:EtOAc=5:1) is used to purify the coarse product and a white solid (1.28 g) is obtained. The yield is 91% and the other analysis includes:

$^1$H NMR (400 MHz, CDCl$_3$)
 δ 1.45-1.49 (m, 2H, ((CH$_2$)$_2$CH$_2$(CH$_2$)$_2$)), 1.55-1.62 (m, 4H, N(CH$_2$CH$_2$)$_2$), 2.47-2.55 (m, 2H, NCH$_2$), 2.62 (br, 2H, NCH$_2$), 3.38 (d, J=4.0 Hz, 1H, NCH), 5.38 (d, J=4.0 Hz, 1H, CHOH), 6.98-7.26 (m, 10H, ArH)

$^{13}$C NMR (100 MHz, CDCl$_3$)
 δ 24.60 ((CH$_2$)$_2$CH$_2$(CH$_2$)$_2$), 26.28 (N(CH$_2$CH$_2$)$_2$), 52.51 (N(CH$_2$)$_2$), 71.55 (NCH), 76.42 (CHOH), 126.14, 126.58, 127.01, 127.42, 129.43, 136.64, 141.38 (2Ph)

IR ν$_{max}$ (cm$^{-1}$) 3131 (OH)

Element analysis C$_{19}$H$_{23}$NO
 theoretical: C,81.10; H,8.24; N,4.98; O,5.68
 experimental: C,81.65; H,8.41; N,4.72; O,5.22

High-resolution MS (70 eV) m/e theoretical: 281.1780
 experimental: 281.1770

[α]$^{25}_D$=−74.2 (c=1.2, CHCl$_3$)

melting point: 93-95° C.

Step (b): Preparing (1R,2S)-1,2-Diphenyl-2-piperidin-1-yl-1-thioacetyl-ethane (7g5b)

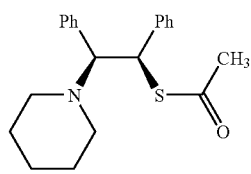

Repeat Step (b) of Example 6, but the compound (6g4a) is replaced with the compound (7g5a). Column chromatography (Silica gel 70 g, eluent is n-Hexane:NEt$_3$=160:1) is used to purify the coarse product and an orange solid (1.46 g) is obtained. The yield is 86% and the other analysis includes:

$^1$H NMR (400 MHz, CDCl$_3$)

δ 1.20 (br, 2H, ((CH$_2$)$_2$CH$_2$(CH$_2$)$_2$)), 1.26 (br, 2H, NCH$_2$CH$_2$), 1.31 (br, 2H, NCH$_2$CH$_2$), 2.14 (s, 3H, COCH$_3$), 2.14 (br, 2H, NCH$_2$), 2.41 (br, 2H, NCH$_2$), 3.82 (d, J=10.4 Hz, 1H, NCH), 5.31 (d, J=10.4 Hz, 1H, SCH), 7.10-7.31 (m, 10H, ArH)

$^{13}$C NMR (100 MHz, CDCl$_3$)

δ 24.42 ((CH$_2$)$_2$CH$_2$(CH$_2$)$_2$), 26.04 (N(CH$_2$CH$_2$)$_2$), 30.49 (COCH$_3$), 48.78 (NCH) 50.71 (N(CH$_2$)$_2$), 73.28 (SCH), 126.67, 127.32, 127.59, 127.81, 128.25, 128.72, 136.03, 141.72 (2Ph)

Element analysis C$_{21}$H$_{25}$NOS theoretical: C,74.29; H,7.42; N,4.13; O,4.71; S9.45 experimental: C,74.19; H,7.10; N,4.49; O,4.52; S9.70 high-resolution MS (70 eV) m/e theoretical: 339.5005 experimental: 339.5436

Step (c): Preparing (1R,2S)-1,2-Diphenyl-2-piperidin-1-yl-ethanethiol (7g5c)

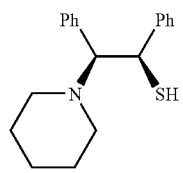

Repeat Step (c) of EXAMPLE 1, but compound (6g4b) is replaced with compound (7g5b). A transparent liquid (0.505 g) is obtained. The yield is 85% and the other analysis includes:

$^1$H NMR (400 MHz, CDCl$_3$)

δ 1.16-1.29 (m, 6H, (CH$_2$(CH$_2$CH$_2$)$_2$N), 2.01 (SH), 2.18 (br, 2H, CH$_2$(CH$_2$CH$_2$)$_2$N), 2.34 (br, 2H, CH$_2$(CH$_2$CH$_2$)$_2$N), 3.78 (d, J=4.8 Hz, 1H, NCH), 4.68 (d, J=4 Hz, 1H, SCH), 7.14-7.30 (m, 10H, ArH)

$^{13}$C NMR (100 MHz, CDCl$_3$)

δ 24.42 ((CH$_2$)$_2$CH$_2$(CH$_2$)$_2$), 26.12 (N(CH$_2$CH$_2$)$_2$), 44.75 (NCH) 50.86 (N(CH$_2$)$_2$), 76.36 (SCH), 126.84, 127.32, 127.61, 127.89, 128.03, 129.22, 135.75, 142.03 (2Ph)

Element analysis C$_{18}$H$_{21}$NS theoretical: C, 76.72; H, 7.79; N, 4.71; S, 10.78 experimental: C, 76.85; H, 7.83; N, 4.75; S, 10.82

High-resolution MS (70 eV) m/e theoretical: 297.1551 experimental: 298.0035

[α]$^{25}$$_D$=−122.0 (c=1, CHCl$_3$)

EXAMPLE 10

Preparation of (1R,2S)-1,2-Diphenyl-2-morpholin-4-yl-ethane-1-thiol (7g6c)

Step (a): Preparing (1R,2S)-1,2-Diphenyl-2-morpholin-4-yl-ethanol (7g6a)

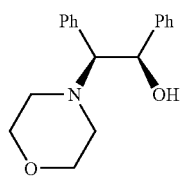

Repeat Step (a) of EXAMPLE 6, but replace (1R,2S)-2-amino-1-phenyl-3-methyl-butanol with (1R,2S)-2-amino-1,2-diphenylethanol, and replace 1,4-dibromobutane with (BrC$_2$H$_4$)$_2$O. Column chromatography (Silica gel 50 g, eluent is n-Hexane:EtOAc=4:1) is used to purify the coarse product and a white solid (1.34 g) is obtained. The yield is 95% and the other analysis includes:

$^1$H NMR (400 MHz, CDCl$_3$)

δ 2.51-2.56 (m, 2H, N(CH$_2$)$_2$), 2.66 (br, 2H, N(CH$_2$)$_2$), 3.30 (s, 1H, OH), 3.36 (d, J=4.0 Hz, 1H, NCH), 3.70-3.76 (m, 4H, O(CH$_2$)$_2$), 5.33 (d, J=4.0 Hz, 1H, CHOH), 6.94-7.26 (m, 10H, ArH)

$^{13}$C NMR (100 MHz, CDCl$_3$)

δ 51.96 (N(CH$_2$)$_2$), 67.11 (O(CH$_2$)$_2$), 71.18 (NCH), 76.44 (CHOH), 126.11, 126.87, 127.40, 127.56, 127.60, 129.54, 135.56, 140.81 (2Ph)

IR ν$_{max}$ (cm$^{-1}$) 3127 (OH)

Element analysis C$_{18}$H$_{21}$NO$_2$ theoretical: C,76.33; H,7.46; N,4.93; O, 11.28 experimental: C,76.38; H,7.36; N,4.90; O,11.36

High-resolution MS (70 eV) m/e theoretical: 283.1573 experimental: 283.1570

[α]$^{25}$$_D$=−140.7 (c=1.4, CHCl$_3$)

melting point: 123-125° C.

Step (b): Preparing (1R,2S)-1,2-Diphenyl-2-morpholin-4-yl-1-thioacetyl-ethane (7g6b)

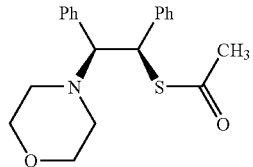

Repeat Step (b) of EXAMPLE 6, but replace compound (6g4a) with compound (7g6a). Column chromatography (Silica gel 70 g, eluent is n-Hexane:NEt$_3$=100:1) is used to purify the coarse product and an orange solid (1.57 g) is obtained. The yield is 92% and the other analysis includes:

$^1$H NMR (400 MHz, CDCl$_3$)

δ 2.20 (s, 3H, COCH$_3$), 2.31-2.35 (m, 2H, N(CH$_2$)$_2$), 2.46 (m, 2H, N(CH$_2$)$_2$), 3.51(m, 4H, O(CH$_2$)$_2$), 3.72 (d, J=8.8 Hz, 1H, NCH), 5.28 (d, J=8.4 Hz, 1H, SCH), 7.05-7.27 (m, 10H, ArH)

$^{13}$C NMR (100 MHz, CDCl$_3$)
 δ 30.58(COCH$_3$), 48.88(NCH), 50.49 (N(CH$_2$)$_2$), 66.95 (O(CH$_2$)$_2$), 73.63(SCH), 126.93, 127.72, 127.78, 127.86, 128.43, 128.94, 135.88, 140.87 (2Ph)

Element analysis C$_{20}$H$_{23}$NO$_2$S
 theoretical: C,70.35; H,6.79; N,4.10; O,9.37; S9.39
 experimental: C,70.85; H,6.14; N,4.69; O,6.17; S9.15

High-resolution MS (70 eV) m/e theoretical: 341.4727
 experimental: 341.4794

Step (c): Preparing (1R,2S)-1,2-Diphenyl-2-morpholin-4-yl-ethane-1-thiol (7g6c)

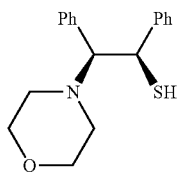

Repeat Step (c) of EXAMPLE 6, but replace compound (6g4b) with compound (7g6b). Column chromatography (Silica gel 40 g, eluent is n-Hexane:NEt$_3$=300:1) is used to purify the coarse product and a white solid (0.31 g) is obtained. The yield is 53% and the other analysis includes:

$^1$H NMR (400 MHz, CDCl$_3$)
 δ 1.96(s, 1H, SH), 2.39-2.46 (m, 4H, N(CH$_2$)$_2$), 3.48-3.56 (m, 4H, O(CH$_2$)$_2$), 3.71 (d, J=8.4 Hz, 1H, NCH), 4.70 (d, J=8.4 Hz, 1H, CHSH), 7.12-7.30 (m, 10H, ArH)

$^{13}$C NMR (100 MHz, CDCl$_3$)
 δ 44.75 (NCH), 50.44 (N(CH$_2$)$_2$), 66.95 (O(CH$_2$)$_2$), 75.87 (CHSH), 127.10, 127.67, 127.94, 128.14, 129.44, 135.10, 141.24 (2Ph)

Element analysis C$_{18}$H$_{21}$NOS
 theoretical: C,72.20; H,7.07; N,4.68; O,5.34; S10.71
 experimental: C,72.33; H,7.12; N,4.47; O,5.33; S10.75

High-resolution MS (70 eV) m/e theoretical: 299.4359
 experimental: 299.4358

[Application Mode 1]

To show effect of the aminothiol of the present invention in addition reactions of organic zinc and aldehyde, diethylzinc (ZnEt$_2$) and benzaldehyde are provided to perform the following reaction:

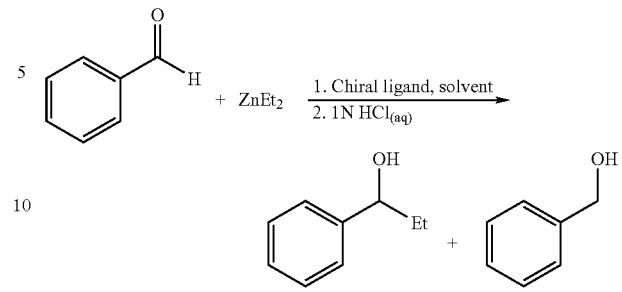

Table 2 lists chiral ligands and conditions applied in the addition reaction. In the application, the chiral ligand obtained in the above EXAMPLEs is added into a dried flask at an equivalence concentration (N$_{lig}$). The flask is then sealed and vacuumed to remove moisture and then filled with nitrogen. Diethylzinc (ZnEt$_2$) dissolved in toluene or hexane is added in the flask at an equivalence concentration (N$_{ZE}$) and a proper temperature. Next, under a specific temperature (T$_{rxn}$), benzaldehyde (0.11 mL, 1.0 mmol) is added into the flask and stirred for a period (t$_{rxn}$). To terminate the reaction, 1N aqueous HCl (1 mL) is added into the above solution. The solution is then extracted with acetyl acetate (20 mL), wherein the organic layer is collected and dehydrated with anhydrous MgSO$_4$, and then the mixture is filtered. The filtrate is concentrated by reducing pressure through an air pump to obtain crude product. The crude product is purified by column chromatography (Silica gel, eluent is n-Hexane: EtOAc=10:1).

HPLC (high-pressure liquid chromatography) with Daicel Chiralcel OD Column is provided for determining enantiomeric excess (e.e.) of the product, wherein the eluent is n-hexane:i-propanol=98.0:2.0, flow rate is 1.5 ml/min. In the above addition reaction of ZnEt$_2$ and various aldehyde, peaks of products are present at different time, as indicated in Table 3. The enantiomeric excess (e.e.) can be determined according to the following equation:

$$\text{e.e.}(\%) = \frac{|S-R|}{S+R} \times 100\%$$

wherein (S+R) in denominator is the product obtained without adding chiral ligands of the present invention;
 S or R in numerator is the product obtained by adding chiral ligands of the present invention.

TABLE 2

| EXAMPLE | Ligand | N$_{lig}$ (meq) | S/C | N$_{ZE}$ (meq) | Solvent | t$_{rxn}$ (h) | T$_{rxn}$ (° C.) | e.e. (%) |
|---|---|---|---|---|---|---|---|---|
| 1 | 6b4c | 0.05 | 20 | 1.2 | Toluene | 12 | −20 | 96.5 R |
| 2 | 2f4c | 0.05 | 20 | 1.2 | Toluene | 12 | −20 | 95.7 R |
| 3 | 6c4c | 0.05 | 20 | 1.2 | Toluene | 12 | −20 | 94.2 R |
| 4 | 3f4c | 0.05 | 20 | 1.2 | Toluene | 12 | −20 | 93.2 R |
| 5 | 6f4c | 0.05 | 20 | 1.2 | Toluene | 12 | −20 | 99.6 R |
|  |  | 0.05 | 20 | 1.2 | Toluene | 6 | rt | 98.5 R |
|  |  | 0.05 | 20 | 1.2 | Toluene | 12 | 0 | 99.3 R |
|  |  | 0.05 | 20 | 1.2 | Toluene | 12 | −20 | 99.6 R |
|  |  | 0.05 | 20 | 1.2 | Hexane | 12 | −20 | 99.2 R |
|  |  | 0.05 | 20 | 1.2 | T/THF | 12 | −20 | 92.1 R |
|  |  | 0.05 | 20 | 1.2 | T/CH2Cl2 | 12 | −20 | 99.5 R |
|  |  | 0.05 | 20 | 1.2 | T/C6H6 | 12 | −20 | 99.6 R |
|  |  | 0.05 | 20 | 2 | Toluene | 12 | −20 | 99.6 R |

TABLE 2-continued

| EXAMPLE | Ligand | $N_{lig}$ (meq) | S/C | $N_{ZE}$ (meq) | Solvent | $t_{rxn}$ (h) | $T_{rxn}$ (°C.) | e.e. (%) |
|---|---|---|---|---|---|---|---|---|
| | | 0.05 | 20 | 3 | Toluene | 12 | −20 | 99.5 R |
| | | 0.05 | 20 | 4 | Toluene | 12 | −20 | 99.5 R |
| | | 0.05 | 20 | 5 | Toluene | 12 | −20 | 99.5 R |
| | | 0.05 | 20 | 1.2 | Toluene | 12 | −40 | 99.7 R |
| | | 0.05 | 20 | 1.2 | Toluene | 24 | −78 | 90.2 R |
| 5 | 6f4c | 0.5 | 2 | 1.2 | Toluene | 12 | −20 | 99.6 R |
| | | 0.2 | 5 | 1.2 | Toluene | 12 | −20 | 99.6 R |
| | | 0.05 | 20 | 1.2 | Toluene | 12 | −20 | 99.6 R |
| | | 0.001 | 1000 | 1.2 | Toluene | 12 | −20 | 99.2 R |
| | | 0.0005 | 2000 | 1.2 | Toluene | 12 | −20 | 98.5 R |
| | | 0.0001 | 10000 | 1.2 | Toluene | 12 | −20 | 96.5 R |
| 6 | 6g4c | 0.05 | 20 | 1.2 | Toluene | 6 | rt | 98.3 R |
| | | 0.05 | 20 | 1.2 | Toluene | 12 | 0 | 99.3 R |
| | | 0.05 | 20 | 1.2 | Toluene | 12 | −20 | 99.5 R |
| | | 0.05 | 20 | 1.2 | Toluene | 12 | −40 | 99.6 R |
| | | 0.05 | 20 | 1.2 | Toluene | 24 | −78 | 88.2 R |
| 7 | 6g5c | 0.05 | 20 | 1.2 | Toluene | 12 | rt | 99.0 R |
| | | 0.05 | 20 | 1.2 | Toluene | 12 | 0 | 99.0 R |
| | | 0.05 | 20 | 1.2 | Toluene | 12 | −20 | 99.6 R |
| | | 0.01 | 100 | 1.2 | Toluene | 12 | −20 | 99.0 R |
| | | 0.001 | 1000 | 1.2 | Toluene | 12 | −20 | 98.1 R |
| | | 0.05 | 20 | 1.2 | Toluene | 12 | −40 | 99.6 R |
| | | 0.05 | 20 | 1.2 | Toluene | 12 | −78 | 93.7 R |
| 8 | 7g4c | 0.1 | 10 | 5 | Toluene | 12 | −20 | 99.3 R |
| | | 0.1 | 10 | 4 | Toluene | 12 | −20 | 99.5 R |
| | | 0.1 | 10 | 3.7 | Toluene | 12 | −20 | 99.5 R |
| | | 0.1 | 10 | 3 | Toluene | 12 | −20 | 99.4 R |
| | | 0.1 | 10 | 2 | Toluene | 12 | −20 | 99.3 R |
| | | 0.1 | 10 | 1.2 | Toluene | 12 | −20 | 99.3 R |
| | | 0.05 | 20 | 1.2 | Toluene | 6 | rt | 99.1 R |
| | | 0.05 | 20 | 1.2 | Toluene | 9 | 0 | 99.2 R |
| | | 0.05 | 20 | 1.2 | Toluene | 12 | −20 | 99.3 R |
| | | 0.05 | 20 | 1.2 | Toluene | 12 | −40 | 99.5 R |
| | | 0.05 | 20 | 1.2 | Toluene | 24 | −78 | 94.2 R |
| | | 0.0002 | 5000 | 3.7 | Toluene | 12 | −20 | 99.0 R |
| | | 0.0005 | 2000 | 3.7 | Toluene | 12 | −20 | 99.1 R |
| | | 0.001 | 1000 | 3.7 | Toluene | 12 | −20 | 99.2 R |
| 8 | 7g4c | 0.003 | 333 | 3.7 | Toluene | 12 | −20 | 99.3 R |
| | | 0.006 | 167 | 3.7 | Toluene | 12 | −20 | 99.3 R |
| | | 0.01 | 100 | 3.7 | Toluene | 12 | −20 | 99.3 R |
| | | 0.02 | 50 | 3.7 | Toluene | 12 | −20 | 99.4 R |
| | | 0.05 | 20 | 3.7 | Toluene | 12 | −20 | 99.4 R |
| | | 0.1 | 10 | 3.7 | Toluene | 12 | −20 | 99.5 R |
| | | 0.2 | 5 | 3.7 | Toluene | 12 | −20 | 99.5 R |
| | | 0.4 | 3 | 3.7 | Toluene | 12 | −20 | 98.8 R |
| 9 | 7g5c | 0.1 | 10 | 3.7 | Toluene | 12 | −20 | 99.7 R |
| | | 0.05 | 20 | 2 | Toluene | 12 | 0 | 99.7 R |
| 10 | 7g6c | 0.1 | 10 | 3.7 | Toluene | 12 | −20 | 99.5 R |

In Table 2, S/C is an equivalence ratio of benzaldehyde (substrate, 1.0 mmol) to the chiral ligand. As shown in Table 2, the chiral ligands of the present invention exhibit superior enantioselectivity in the asymmetric of benzaldehyde and diethyl zinc, even as S/C are very high. For example, when compounds (6f4c), (6g5c) and (7g4c) obtained from EXAMPLEs 5, 7 and 8 are applied at S/C as high as 1,000, enantiomeric excess are more than 98%. Therefore, aminothiol compounds in the present invention are indeed very economic for applying the above asymmetric reactions to industries.

Table 3 list more aminothiol compounds with various ligands and application results thereof in varied reaction conditions. These aminothiol compounds can be produced through similar procedures of above EXAMPLEs by supplying proper reactants having respective ligands. Therefore, detailed description is omitted in the specification.

In Table 3, Compound (5g3c) has the following formula.

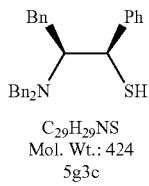

$C_{29}H_{29}NS$
Mol. Wt.: 424
5g3c

The related analysis of Compound (5g3c) include:

$^1$H NMR (400 MHz, CDCl$_3$)

δ 3.04-3.22(m, 2H, PhCH$_2$), 3.503.60 (m, 1H, CNH), 3.60 (s, 4H, PhCH$_2$N), 4.37 (t, J=4.0 Hz, 1H, PhCHS), 6.81-7.41 (m, 20H, ArH)

$^{13}$C NMR (100 MHz, CDCl$_3$)

δ 24.68, 26.53, 46.06, 51.41, 72.86, 125.83, 126.81, 127.94, 128.10, 128.14, 129.31, 140.85, 143.663.

Element analysis $C_{29}H_{29}NS$

TABLE 3

| Ligand | $N_{lig}$ (meq) | S/C | $N_{ZE}$ (meq) | Solvent | $t_{rxn}$ (h) | $T_{rxn}$ (° C.) | e.e. (%) |
|---|---|---|---|---|---|---|---|
| 2g5c | 0.05 | 20 | 2 | Hexane | 12 | 0 | 100.0 R |
| | 0.05 | 20 | 1.2 | Toluene | 12 | rt | 91.0 R |
| | 0.05 | 20 | 1.2 | Toluene | 12 | 0 | 97.9 R |
| 4g5c | 0.0005 | 2000 | 1.2 | Toluene | 12 | −20 | 97.7 R |
| | 0.0001 | 10000 | 1.2 | Toluene | 12 | −20 | 98.1 R |
| | 0.005 | 200 | 1.2 | Toluene | 12 | −20 | 98.1 R |
| | 0.001 | 1000 | 1.2 | Toluene | 12 | −20 | 98.1 R |
| | 0.05 | 20 | 1.2 | Toluene | 12 | −20 | 98.9 R |
| | 0.1 | 10 | 1.2 | Toluene | 12 | −20 | 98.9 R |
| | 0.2 | 5 | 1.2 | Toluene | 12 | −20 | 98.8 R |
| | 0.05 | 20 | 1.2 | Toluene | 12 | −40 | 99.3 R |
| 5g2c | 0.05 | 20 | 1.2 | Toluene | 12 | rt | 96.9 R |
| 5g3c | 0.05 | 20 | 1.2 | Toluene | 12 | 0 | 93.5 R |
| 5g4c | 0.05 | 20 | 1.2 | Toluene | 12 | 0 | 98.9 R |
| 5g5c | 0.05 | 20 | 5 | Toluene | 12 | 0 | 99.1 R |
| | 0.05 | 20 | 4 | Toluene | 12 | 0 | 99.4 R |
| | 0.05 | 20 | 3 | Toluene | 12 | 0 | 99.4 R |
| | 0.05 | 20 | 2 | Toluene | 12 | 0 | 99.3 R |
| | 0.05 | 20 | 1.2 | Toluene | 12 | 0 | 99.3 R |
| | 0.05 | 20 | 1.1 | Toluene | 12 | 0 | 99.3 R |
| | 0.05 | 20 | 1.2 | Hexane | 12 | 0 | 99.1 R |
| | 0.05 | 20 | 1.2 | T/CH2Cl2 | 12 | 0 | 99.1 R |
| | 0.05 | 20 | 1.2 | T/THF | 12 | 0 | 72.0 R |
| | 0.0001 | 10000 | 1.2 | Toluene | 12 | 0 | 98.1 R |
| | 0.0002 | 5000 | 1.2 | Toluene | 12 | 0 | 98.9 R |
| 5g5c | 0.0005 | 2000 | 1.2 | Toluene | 12 | 0 | 99.0 R |
| | 0.001 | 1000 | 1.2 | Toluene | 12 | 0 | 99.1 R |
| | 0.002 | 500 | 1.2 | Toluene | 12 | 0 | 99.1 R |
| | 0.005 | 200 | 1.2 | Toluene | 12 | 0 | 99.2 R |
| | 0.01 | 100 | 1.2 | Toluene | 12 | 0 | 99.3 R |
| | 0.02 | 50 | 1.2 | Toluene | 12 | 0 | 99.3 R |
| | 0.05 | 20 | 1.2 | Toluene | 12 | 0 | 99.3 R |
| | 0.1 | 10 | 1.2 | Toluene | 12 | 0 | 99.4 R |
| | 0.2 | 5 | 1.2 | Toluene | 12 | 0 | 99.4 R |
| | 0.5 | 2 | 1.2 | Toluene | 12 | 0 | 99.4 R |
| | 1 | 1 | 1.2 | Toluene | 12 | 0 | 99.0 R |
| | 0.05 | 20 | 1.2 | Toluene | 3 | rt | 98.1 R |
| | 0.05 | 20 | 1.2 | Toluene | 12 | 0 | 99.3 R |
| | 0.05 | 20 | 1.2 | Toluene | 18 | −20 | 99.4 R |
| | 0.05 | 20 | 1.2 | Toluene | 24 | −40 | 99.4 R |
| | 0.05 | 20 | 1.2 | Toluene | 48 | −78 | 87.9 R |
| | 0.05 | 20 | 1.2 | Toluene | 0.5 | rt | 97.8 R |
| | 0.05 | 20 | 1.2 | Toluene | 1 | rt | 98.1 R |
| | 0.05 | 20 | 1.2 | Toluene | 1.5 | rt | 98.1 R |
| 5g5c | 0.05 | 20 | 1.2 | Toluene | 3 | rt | 98.1 R |
| | 0.05 | 20 | 1.2 | Toluene | 6 | rt | 98.1 R |
| 5g6c | 0.05 | 20 | 1.2 | Toluene | 12 | 0 | 98.2 R |
| 6g1c | 0.05 | 20 | 1.2 | Toluene | 12 | −20 | 97.7 R |
| 6g2c | 0.05 | 20 | 1.2 | Toluene | 12 | −20 | 99.4 R |
| 6g6c | 0.05 | 20 | 1.2 | Toluene | 12 | 0 | 99.1 R |
| | 0.05 | 20 | 1.2 | Toluene | 12 | −20 | 99.4 R |

As shown in Table 3, the aminothiol compounds of the present invention indeed perform excellent catalysts to obtain high enantiomeric excess in the asymmetric addition reaction of benzaldehyde and diethyl zinc.

Similarly, the aminothiol compounds of the present invention can be provided as chiral ligands to react with other organic metals, for example, Cu, to form organometal complexes. These complexes can also react with carbonyl such as aldehyde, to produce alcohol in the asymmetric addition reactions.

[Application Mode 2]

The aminothiol compounds of the present invention also show superior effect in catalyzing an addition reaction as follows:

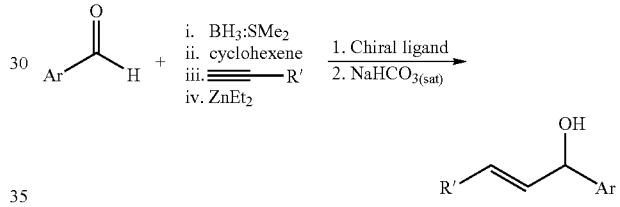

In this reaction, butyl acetylene (or hexyl acetylene), diethylzinc ($ZnEt_2$) and aldehyde are reacted to produce allyl alcohol in existence of chiral ligands of the present invention. Table 4 lists conditions and results of the reaction catalyzed with different ligands including Compound (6g5c) obtained in Example 7, Compound (7g5c) obtained in Example 9, Compound (7g6c) obtained in Example 10 and Compound (6f5c).

TABLE 4

| Ligand | Ar | R' | Mole % of ligand | $T_{rxn}$ (° C.) | $N_{ZE}$ (eq) | $t_{rxn}$ (h) | Conversion (%) | Yield (%) | e.e (%) |
|---|---|---|---|---|---|---|---|---|---|
| 6f5c | Ph | $C_4H_9$ | 5(T) | −10 | 2 | 15 | 100 | 89 | 91.3(R) |
| | Ph | $C_4H_9$ | 5(T) | −20 | 2 | 15 | 100 | 94 | 99.0(R) |
| | Ph | $C_4H_9$ | 5(T) | −20 | 2 | 15 | 100 | 94 | 98.3(R) |
| | Ph | $C_4H_9$ | 1(T) | −30 | 2 | 15 | 100 | 90 | 94.3(R) |
| | Ph | $C_4H_9$ | 2(T) | −30 | 2 | 15 | 100 | 92 | 94.5(R) |
| | Ph | $C_4H_9$ | 5(T) | −30 | 2 | 15 | 100 | 94 | 98.2(R) |
| | Ph | $C_6H_{13}$ | 2(T) | −30 | 2 | 15 | 100 | 65 | 99.0(R) |
| | 4-OMe—Ph | $C_6H_{13}$ | 2(T) | −30 | 2 | 15 | 100 | 90 | 98.1(R) |
| | 2-Cl—Ph | $C_6H_{13}$ | 2(T) | −30 | 2 | 15 | 100 | 86 | 92.6(R) |
| | Ph | $C_6H_{13}$ | 2(H) | −30 | 2 | 15 | 100 | 80 | 99.0(R) |
| | Ph | $C_4H_9$ | 5(T) | −30 | 2 | 15 | 100 | 94 | 98.2(R) |
| | 2-Cl—Ph | $C_4H_9$ | 5(T) | −30 | 2 | 15 | 100 | — | 98.1(R) |
| | Ph | $C_6H_{13}$ | 5(T) | −30 | 2 | 15 | 100 | — | 99.4(R) |
| | Ph | $C_4H_9$ | 5(T) | −40 | 2 | 15 | 100 | 94 | 98.3(R) |
| | Ph | $C_4H_9$ | 15(T) | −30 | 2 | 15 | 100 | — | 99.5(R) |
| 6g5c | Ph | $C_4H_9$ | 5(T) | −30 | 2 | 15 | 100 | 92 | 96.1(R) |
| | Ph | $C_6H_{13}$ | 2(T) | −30 | 2 | 15 | 100 | 92 | 98.6(R) |
| 7g5c | Ph | $C_4H_9$ | 5(T) | −30 | 2 | 15 | 100 | 91 | 95.6(S) |
| | Ph | $C_4H_9$ | 5(T) | −30 | 2 | 15 | 100 | 93 | 97.0(R) |

TABLE 4-continued

| Ligand | Ar | R' | Mole % of ligand | $T_{rxn}$ (° C.) | $N_{ZE}$ (eq) | $t_{rxn}$ (h) | Conversion (%) | Yield (%) | e.e (%) |
|---|---|---|---|---|---|---|---|---|---|
|  | Ph | $C_6H_{13}$ | 2(T) | −30 | 2 | 15 | 100 | 93 | 98.4(R) |
|  | Ph | $C_6H_{13}$ | 5(T) | −30 | 2 | 15 | 100 | 68 | 98.3(R) |
| 7g6c | Ph | $C_4H_9$ | 5(T) | −30 | 2 | 15 | 100 | 95 | 97.3(R) |

In Application Mode 2, ZnEt$_2$ and aldehyde are respectively added by syringe pump over 20 minutes. T and H in the column (mole % of ligand) are the solvents toluene and hexane. Detailed procedures may be referred to Wolfgang Oppolzer et al. (J. Org. Chem. 2001, 66, 4766-4770) and Brase S. et al. (Org. Lett. 2001, 3, 4119). Enantiometric access is determined with HPLC (Chiralcel OD-H column, flow rate 0.7 ml/min, 3% isopropanol).

It should be noticed that the above embodiments are only used for explaining the present invention, but not limiting the scope.

What is claimed is:

1. An aminothiol compound, having a structural formula selected from the group consisting of:

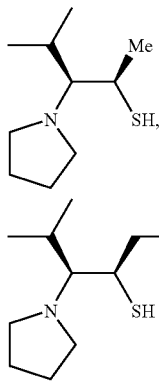
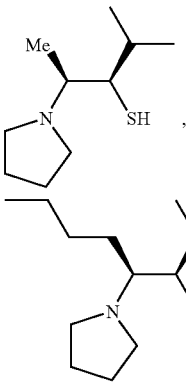
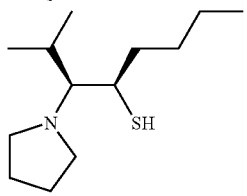

-continued

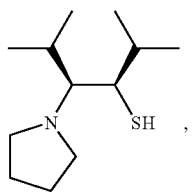
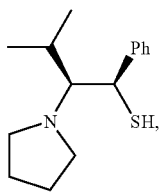
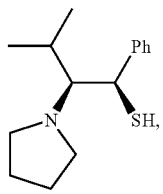
and
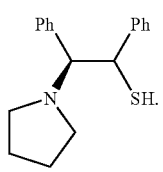

2. The aminothiol compound as claimed in claim 1, which is used for catalyzing an asymmetric addition reaction of an organic metal compound and aldehyde.

3. The aminothiol compound as claimed in claim 2, wherein said organic metal is Zn or Cu.

* * * * *